United States Patent

Smith et al.

[11] Patent Number: 5,811,824
[45] Date of Patent: Sep. 22, 1998

[54] METHOD AND AN APPARATUS FOR TESTING WHETHER A DIAMOND HAS A LAYER OF SYNTHETIC DIAMOND DEPOSITED THEREON

[75] Inventors: Martin Phillip Smith, Wargrave; James Gordon Charters Smith, High Wycombe; Martin Cooper, Marlow, all of United Kingdom

[73] Assignee: Gersan Establishment, Vaduz, Liechtenstein

[21] Appl. No.: 682,543

[22] PCT Filed: Jan. 25, 1995

[86] PCT No.: PCT/GB95/00139

§ 371 Date: Sep. 23, 1996

§ 102(e) Date: Sep. 23, 1996

[87] PCT Pub. No.: WO95/20152

PCT Pub. Date: Jul. 27, 1995

[30] Foreign Application Priority Data

Jan. 25, 1994 [GB] United Kingdom .................... 9401354

[51] Int. Cl.⁶ .................................................. G01N 21/86
[52] U.S. Cl. ........................................... 250/559.4; 356/30
[58] Field of Search ..................... 250/228, 226, 250/221, 559.4, 559.45; 356/30, 376

[56] References Cited

U.S. PATENT DOCUMENTS

| | | | |
|---|---|---|---|
| 4,125,770 | 11/1978 | Lang | 356/30 |
| 4,152,069 | 5/1979 | Bruck | 356/30 |
| 4,259,011 | 3/1981 | Crumm et al. | 356/30 |
| 4,508,449 | 4/1985 | Okazaki | 356/30 |
| 5,118,181 | 6/1992 | Yifrach et al. | 356/30 |
| 5,164,586 | 11/1992 | Hohberg et al. | 356/30 |

FOREIGN PATENT DOCUMENTS

| | | |
|---|---|---|
| 0458223 | 11/1991 | European Pat. Off. . |
| 2528580 | 12/1982 | France . |
| 1598735 | 4/1971 | Germany . |
| 3600115 | 7/1987 | Germany . |
| 2215041 | 9/1989 | United Kingdom . |
| 2267147 | 11/1993 | United Kingdom . |
| WO83/00389 | 2/1983 | WIPO . |
| WO91/16617 | 10/1991 | WIPO . |

*Primary Examiner*—Que Le
*Attorney, Agent, or Firm*—Ostrolenk, Faber, Gerb & Soffen, L.L.P.

[57] ABSTRACT

In order to test whether a diamond 2 comprises synthetic diamond material, a plurality of different zones of the diamond 2 are irradiated with radiation substantially of wavelength substantially 230 nm to 320 nm, an image or reading of the radiation transmitted by each zone of the diamond 2 being produced.

26 Claims, 3 Drawing Sheets

METHOD AND AN APPARATUS FOR TESTING WHETHER A DIAMOND HAS A LAYER OF SYNTHETIC DIAMOND DEPOSITED THEREON

BACKGROUND TO THE INVENTION

The present invention relates to a method of and apparatus for testing whether a diamond has had a layer of synthetic diamond deposited thereon. This is of particular importance in testing whether the diamond comprises CVD diamond material and also in locating such material if present.

Synthetic diamond material may be deposited on an uncut natural diamond which is then worked, for example, into a round brilliant cut. Alternatively, the synthetic diamond material coating may be deposited onto a fully fashioned brilliant stone after working of the stone. The thickness of the synthetic diamond material layer may be very thin (it could be in the range from 5 µm to 10 µm) but the present invention may also be used to detect thicker layers.

The value of a diamond is in part dependent upon its weight. Accordingly, synthetic diamond material may be deposited onto natural gem diamonds, before or after cutting of the diamond, to increase the weight of the finished product.

However, the value of a diamond also resides in its qualities of authenticity and uniqueness and in the fact that it is an entirely natural product. Thus, a diamond that has not been enlarged by deposition of synthetic diamond material has a value over a diamond which has.

Over the years, a number of methods of synthesising diamond material have been developed. One of these methods is the chemical vapour deposition (CVD) technique, which is a low pressure technique involving deposition of synthetic diamond (referred to as CVD diamond material in this specification) onto a substrate from a gas. CVD is the most likely way in which synthetic diamond will be deposited on a diamond. A diamond artificially enlarged by deposition of CVD diamond material is referred to in this specification as a "CVD/natural diamond doublet".

CVD diamond material may be deposited on a non-diamond or diamond substrate. In the latter case, the CVD diamond material can replicate the structure of the diamond substrate (referred to "homoepitaxial growth"). The CVD/natural diamond doublet produced can be identical in appearance, density and other common physical properties to an entirely natural stone and there may be a problem in identifying such a CVD/natural diamond doublet.

It is an object of the present invention to provide a method of and apparatus for testing whether a diamond has had a layer of synthetic diamond deposited thereon.

It is desired that the apparatus should be simple and inexpensive and may be put into operation by a person with relatively little training. The method and apparatus should be capable of being operated reliably and consistently by a practised jeweller who has no training in laboratory gemological analysis.

THE INVENTION

The present invention provides a method of and apparatus for testing whether a diamond has had a layer of synthetic diamond deposited thereon, as set forth in claim 1, 16 and 26. Claims 2 to 15 and 17 to 25 set forth preferred and/or optional features of the invention.

The present inventors have discovered that where different zones of a diamond show differences in their absorption of radiation substantially of wavelength substantially 230 nm to 320 nm, it may be concluded that the diamond in question has had a layer of synthetic diamond deposited thereon. An imaging apparatus or integrating sphere is found to be suitable for investigating a diamond in this way.

The present inventors have further discovered that if all zones of a diamond strongly absorb radiation substantially of wavelength substantially 230 nm to 320 nm, the diamond may be classified as almost certainly a wholly natural diamond.

This is based upon the observation that the majority of natural diamonds are classified as type IaA or IaAB and very strongly absorb ultraviolet radiation of wavelength shorter than approximately 320 nm, whereas a synthetic diamond layer will normally be of a type which strongly absorbs ultraviolet radiation of wavelength shorter than approximately 230 nm, in particular type II.

A very small number of diamonds will fail to be classified as set out above, and may be subjected to a detailed gemmological analysis.

It may be sufficient to test only a few zones (maybe only two) in order to detect a difference in the absorption of the radiation in different zones. Preferably, however, a large number of zones are observed.

The diamond is irradiated with suitable radiation (as discussed below) for example by the following methods.

One side of the diamond may be irradiated diffusely, for example by a lamp. The radiation transmitted by a zone of the diamond may then be observed by imaging the diamond. Alternatively, a fibre optic probe may be placed in contact with a plurality of zones, as set out below.

The diamond may be placed in an irradiated integrating enclosure, such as an integrating sphere, the intensity of radiation transmitted by a given zone of the diamond being detected by a light guide such as a fibre optic probe in contact with that zone. The radiation must pass through the zone of the diamond tested before reaching a detector via the light guide.

The diamond may be irradiated using a beam of confined dimensions which may be produced, for example by an aperture between the diamond and the radiation source. A beam of confined dimensions may be produced by a light guide such as a fibre optic probe and applied to a plurality of different zones of the diamond.

A beam of radiation of confined dimensions may be applied to different zones of the diamond in succession, or a plurality of such beams may be applied to different zones simultaneously.

Preferably, the diamond is placed with the zone of interest in contact with the aperture or with the end of the light guide. If the diamond is not placed directly in contact with the aperture or guide, reflection from the surfaces can occur. This may be overcome by using polarising filters in the irradiating and imaging systems to block reflected light.

The confined beam may be of variable dimension or of fixed dimension. It may correspond in size to a facet of a worked diamond or to a part of a facet. Preferably, the confined beam is smaller than the maximum dimension of the diamond, or is adjustable in size to allow this.

Where the diamond is irradiated using a beam of confined dimensions, the radiation transmitted by the zone may be observed by viewing the diamond against a dark background, by collecting transmitted radiation using a light guide such as a fibre optic probe, by placing the diamond in an integrating enclosure such as an integrating sphere and observing the luminous flux intensity in the enclosure, or by any other suitable means.

An aperture between the diamond and the radiation source could be 2 to 15 mm across, depending on stone size, being suitably 5 to 10 mm. An iris aperture may be provided, adjustable in size to obtain the best image. The apparatus may be suitable for automation.

It can be seen from the above that a fibre optic probe may be used in method of the invention either to irradiate a zone of the diamond or to collect radiation from a zone of the diamond, or both. They can thus be used so as to test only the part of the surface they contact. In either case, the fibre optic probe may be fixed in a mounting for the diamond, different zones of the diamond being placed in contact with the end of the probe by manipulating the diamond. Manipulating means may be provided, for example to allow a diamond to be manipulated in a light sealed box without having to open the box. Alternatively, the diamond may be stationary and the fibre optic probe may be manipulated around the diamond. The end of the fibre optic probe may be of size 1 to 10 mm in diameter, suitably 2 to 4 mm.

A plurality of fibre optic probes may be used for contacting different zones of the diamond at the same time. If the integrating enclosure is irradiated, the fibre optic probes may be used to observe radiation transmitted by the zones simultaneously or in turn.

In order to avoid possible errors arising from poor or uncontrolled contact of the fibre optic probe with a zone of the diamond, a plurality of observations at the same wavelength may be obtained (preferably very quickly) for the same zone and combined statistically to provide a statistically improved reading. Optical means may be provided to allow a visible check to ensure that the end of the probe is in contact with the desired zone of the diamond before the diamond is irradiated with the first mentioned radiation.

The radiation observed could comprise a narrow band of wavelengths lying substantially in the above mentioned range, a number of such narrow bands or it could be a relatively broad band. Optionally, it falls substantially in the range 230 nm to 300 nm. The radiation observed may comprise some radiation of wavelength falling outside the range 230 nm to 320 nm. Radiation of wavelength less than 230 nm will be absorbed by all types of diamond and will not provide useful information. Radiation of wavelength greater than 320 nm will be transmitted with varying degrees of attenuation by all types of diamond, will provide no information and will reduce the contrast of the observations of CVD or natural diamond material.

The radiation observed should be substantially in the abovementioned range; that is, the proportion of radiation of wavelength greater than substantially 320 nm to radiation falling in the range substantially 320 nm to 230 nm should be such that radiation transmitted by CVD diamond material and by natural diamond material is distinguishable. A cut-off filter passing radiation only in the range below substantially 320 nm may be provided between the diamond and the observer.

Preferably, the radiation is generated by a broad band ultraviolet source with a high yield in the range 230 to 320 nm. This ensures an efficient use of energy from a relatively inexpensive source.

Preferably, the radiation is generated by a mercury lamp, the 254 nm band of the mercury lamp being most prefered.

In order to observe radiation substantially of wavelength substantially 230 nm to 320 nm, the diamond may be irradiated with such radiation. Alternatively, the diamond may be irradiated with radiation of a broader range of wavelengths, wavelength selective means such as a filter being provided between the diamond and the observer to pass radiation of wavelength substantially 230 nm to 320 nm. If the diamond is irradiated with radiation substantially of wavelength substantially 230 nm to 320 nm, wavelength selective means may also be provided to exclude radiation produced by fluorescence excited by the incident ultraviolet radiation. Normally, however, the intensity of fluorescence is not strong enough to require filtering.

When the irradiating radiation is incident on a zone of the diamond, it will generally be strongly absorbed or partially transmitted. The radiation transmitted by a zone of the diamond will be refracted inside the diamond and some transmitted radiation may be observed leaving the surface of the diamond. Natural diamond usually has such a high absorption coefficient at the wavelengths in question that incident radiation is totally absorbed. No transmitted radiation will be observed leaving the surface for such zones. CVD or other synthetic diamond material surface layers are commonly of a type that at least partially transmits the radiation, in particular type II diamond.

The radiation path within a diamond is complex, due to the configuration of the facets and the high refractive index of diamond. However, some radiation will be transmitted to surfaces of the diamond, opposite or adjacent the point of irradiation for example. The radiation can then be observed by, for example, a detector combined with a radiation collector (such as a light guide such as a fibre optic pick-up probe or integrating enclosure such as an integrating sphere) or it can be imaged.

Forming an image of the diamond is efficient and easy to interpret. Several images may have to be formed, to check all zones of the diamond, because the radiation leaving the surface of the zone irradiated will not be observed if it is not in the field of view of the imaging system.

A very thin layer of CVD diamond material may be difficult to detect. Normally, the radiation leaving the surface of a layer of CVD diamond material of thickness greater than about 100 $\mu$m or 150 $\mu$m may be imaged with an ultraviolet sensitive camera with normal magnification. However, if the camera is used with an ultraviolet microscope, CVD layers of thicknesses as small as 5 to 10 $\mu$m could be imaged.

Where ordinary resolution is sufficient, an ultraviolet image could be formed on an ultraviolet conversion phosphor screen, which converts the ultraviolet image into a visible image, which is then viewed by a simple optical system.

Because of the complex pattern of light paths within a brilliant-cut diamond, the two parts of a CVD/natural diamond doublet may not be immediately apparent. It may be necessary to manipulate a CVD/natural diamond doublet while it is being viewed, in order to clearly see the two parts of the diamond.

If a transmissive surface is not irradiated, it cannot be detected. Therefore, it is preferred that the image of the diamond is formed using different directions of irradiation.

The imaging means preferably forms an image of the whole of one side of the diamond, but it could be set up to image only an area of the diamond which includes the zone irradiated or it could be set up with variable magnification so that it can zoom in on such an area.

The diamond may be imaged against a light background, non transmissive zones appearing dark and transmissive zones appearing light. Alternatively, the diamond may be imaged against a dark field, in which case radiation leaving the surface of a transmissive zone will show up strongly. Normally, when the diamond is viewed against a dark field, it is imaged in a direction different to the direction of irradiation.

In order to assist in the interpretation of the patterns of transmissive and non-transmissive zones revealed by a simple image of the diamond when irradiated with the first mentioned radiation, the diamond may be irradiated with radiation which is substantially transmitted by all types of diamond, such as visible radiation, or which is transmitted by no type of diamond, such as radiation of wavelength less than 230 nm, so that an image of the entire diamond (or reference image) may be formed. This reference image may then be compared to an image taken using the first mentioned radiation, preferably with the diamond in the same configuration.

If a mercury lamp is used, the reference radiation may comprise the 365 nm band of the mercury lamp. In some cases, although a zone will transmit radiation, no transmitted radiation will be observed, because of internal reflection within the diamond. Features caused by ultraviolet absorption may be distinguished from artifacts caused by internal reflection by using the reference image. Such a reference image may be used when the diamond is imaged against a dark background or against a light background.

In an alternative embodiment, the reference image may be formed by forming an image of light reflected from the surface of the stone. Mounting means may be provided for allowing the diamond to be placed in different positions with respect to the irradiating means or imaging means, to facilitate the taking of images in different directions or with different directions of irradiation.

The apparatus according to the invention could be automated to automatically interpret and analyse images or readings produced. However, this is not preferred, as a simple system in which the images are interpreted by the operator is practicable and cheaper.

The invention will be further described by way of example only, with reference to the accompanying drawings, in which:

DETAILED DESCRIPTION OF THE DRAWINGS

Figure 1:
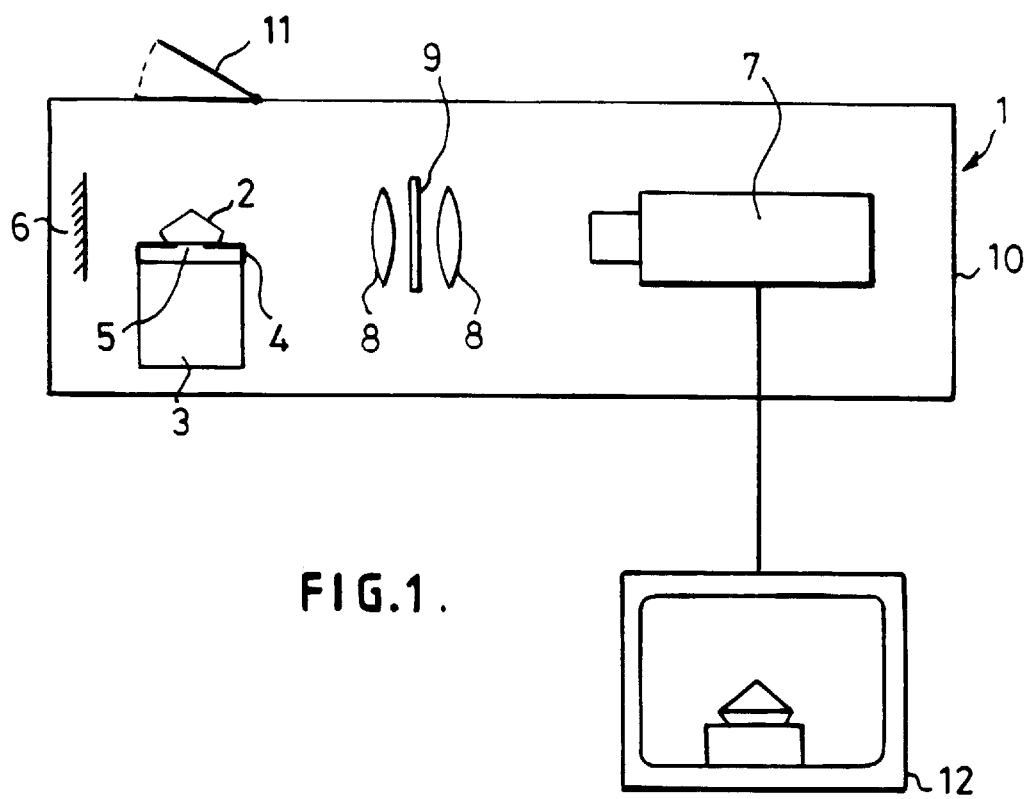
FIG. 1 is a schematic diagram of an apparatus according to a first embodiment of the invention.

FIG. 1 shows an apparatus 1 according to the invention. A diamond 2 is shown resting on means for irradiating the diamond, in the form of an ultraviolet light source 3 having means 4 for defining an aperture 5. The zone of the diamond above the aperture 5 only is irradiated. Means 6 are provided for defining a dark background against which the diamond 2 is imaged by image forming means in the form of an ultraviolet sensitive TV camera 7. An ultraviolet transmitting lens system 8 is provided and an ultraviolet filter 9 for transmitting only ultraviolet radiation lying in the range 230 nm to 320 nm. The apparatus is encased in a casing 10 to prevent potentially harmful radiation leaking out. A door 11 is provided in the casing 10 to allow the diamond 2 to be manipulated. A TV monitor 12 produces an image of the diamond for observation.

The TV camera 7 may comprise a CCD camera. A phosphor screen could be placed at the focus of the lens system 8 for direct observation of the image, but this is not preferred. The image can be built up normally or by a raster scan. If necessary, photographic film could be used to record the image produced by the lens system 8.

Figure 2A:
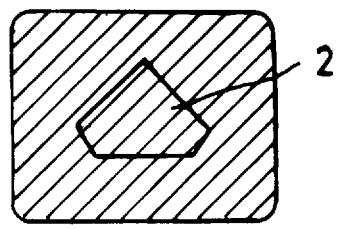
FIGS. 2a and 2b show a schematic illustrations of the image of a natural stone and of a CVD/natural diamond doublet respectively as produced by the apparatus of FIG. 1.
Figure 2B:
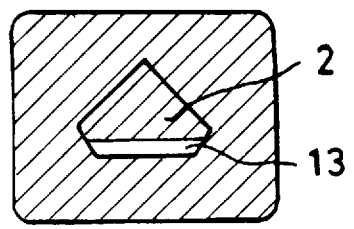

In use, the ultraviolet source 3 is switched on so that the zone of the diamond 2 in contact with the aperture 5 is irradiated. Any radiation transmitted by this zone is imaged against the background 6 by the camera 7 and displayed on the TV monitor 12. If an entirely dark image of the diamond is observed, as shown in FIG. 2a, the zone in contact with the aperture is classified as natural diamond. If, however, a bright zone on the image of the diamond is observed, as shown in FIG. 2b, the bright zone is classified as CVD diamond material 13.

The diamond 2 may have to be manipulated on aperture 5 in order that all zones of the diamond be irradiated.

Figure 3:
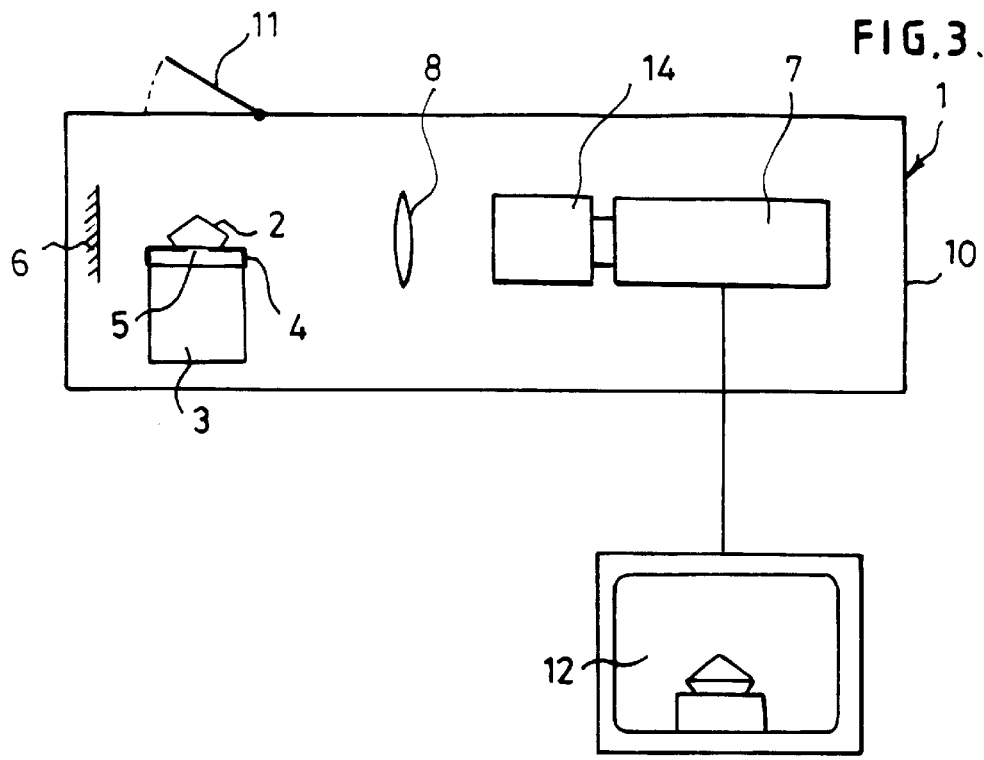
FIG. 3 schematically shows a second embodiment of apparatus according to the invention.

FIG. 3 shows a similar apparatus to FIG. 1, like numerals indicating like parts. However, a simple single lens system 8 is used, an image intensifier unit 14 with a solar blind response photocathode being provided in front of the camera 7. This takes the place of the ultraviolet filter 9 and only responds to radiation in the range 225 nm to 350 nm. Accordingly, the amount of radiation outside the range 230 nm to 320 nm will not normally be sufficient to swamp the image. The image intensifier unit provides a standard monochrome image to camera 7. The images produced by the apparatus of FIG. 3 correspond to those shown in FIGS. 2a and 2b.

Figure 4:
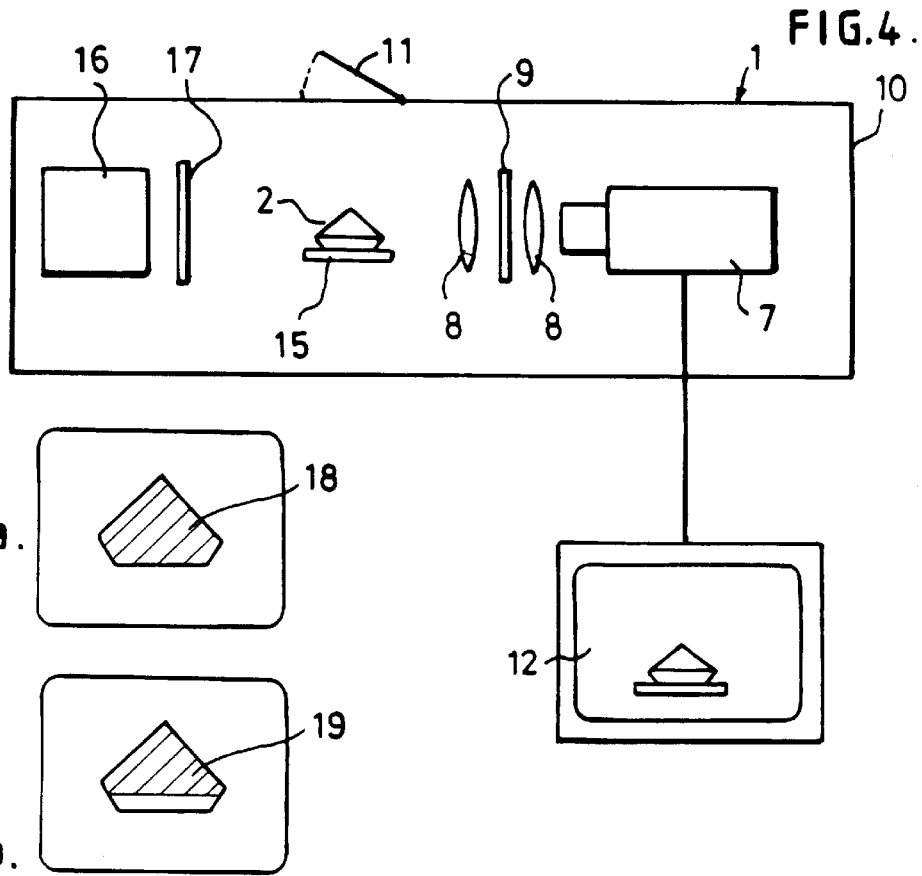
FIG. 4 schematically shows a third embodiment of apparatus according to the invention.
Figure 5A:
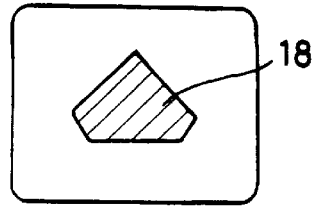
FIGS. 5a and 5b show schematic illustrations of images produced by the apparatus of FIG. 4 with a natural diamond and a CVD/natural diamond doublet respectively.
Figure 5B:
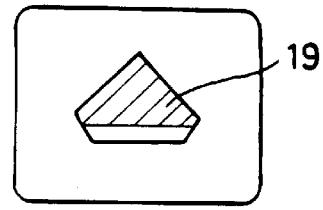

The apparatus shown in FIG. 4 is set up to produce an image of the diamond as seen against a light background. The apparatus comprises a lens system 8, ultraviolet filter 9 (which may be replaced by an image intensifier as shown in FIG. 3), a TV camera 7 and a monitor 12 all encased in a casing 10 with a door 11, as in FIG. 1. However, the diamond 2 is mounted on a plinth 15 and is illuminated by a light source 16 which comprises a diffusing screen 17 so that the diamond is imaged against a uniform light background. The images produced by the apparatus of FIG. 4 are shown in FIGS. 5a and 5b. A dark image as shown in FIG. 5a indicates that there is no CVD diamond material visible, whereas a bright zone as shown in FIG. 5b indicates a CVD zone transmitting a portion of the incident light and hence a CVD/natural diamond doublet 19.

In order to place the CVD part in the correct configuration, it may be necessary to manipulate the diamond 2 and place it in a number of positions on the plinth 15 until all positions have been tried.

Figure 6:
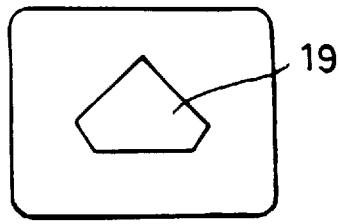
FIG. 6 shows a schematic illustration of the image of a diamond produced, using the apparatus of FIG. 1, 3 or 4, using the further radiation.

In order to provide a reference image for locating CVD parts using the apparatus of FIG. 1, 3 or 4, the light source 3 or 16 may be switched from ultraviolet operation to operation at a wavelength which is either totally absorbed by all types of diamond or substantially transmitted by all types of diamond. For example, visible light may be used. This will produce an image generally as shown in FIG. 6, with all parts of the diamond 18 or 19 being visible, (facets of the diamond may be apparent in the image due to internal reflection and refraction, but have not been shown in the figure, for clarity). The diamond material is, of course, transparent to visible radiation, but the image will appear slightly dark, due to refraction of the incident light out of the optical axis of the imaging system 7.

A "frame store" image processing system may be provided, whereby the image with the first mentioned radiation can be compared directly on the screen with the image using the further radiation.

Figure 7:
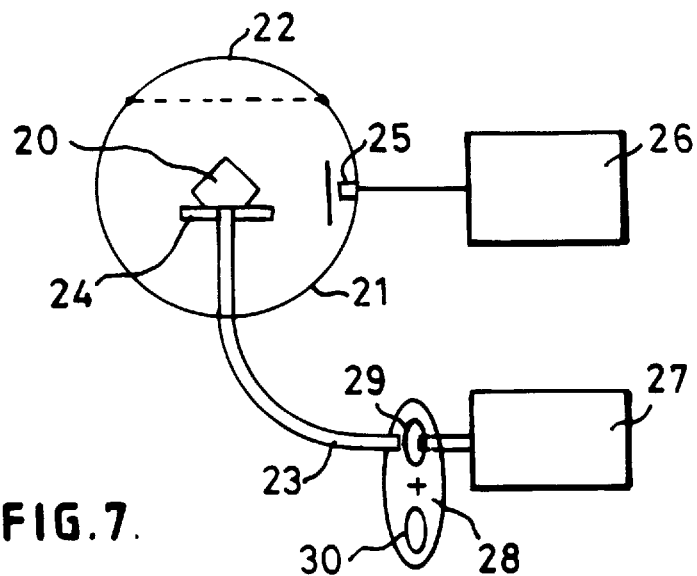
FIG. 7 shows a fourth embodiment of apparatus according to the invention.

FIG. 7 shows a fourth embodiment of the invention. In this embodiment, no image of the diamond is formed. Instead, the diamond 20 is placed in an integrating sphere 21. The top part 22 of the integrating sphere is removeable, in order to allow manipulation of the diamond 20. Radiation of a wavelength falling in the range 230 nm to 320 nm is delivered to the diamond 20 through a fibre optic probe 23 which emerges through a plinth 24. The zone of the diamond 20 which is in contact with the end of the fibre optic probe 23 is irradiated. The fibre optic probe 23 may be manipulated around the diamond 20. A radiation source 27 such as a mercury lamp is provided. A filter wheel 28 is provided having a filter 29 to select a narrow band of wavelengths falling in the above range. For example the 254 nm band of the mercury lamp may be selected.

The end of the probe 23 may comprise a resilient rubber 'boot' to ensure a light-tight contact between it and the diamond. The plinth 24 may be made transparent to the irradiating radiation. A detector 25 such as a photomultiplier tube combined with a filter (to filter out fluorescence or unwanted irradiating radiation) is provided for measuring the luminous flux density in the integrating sphere 21. Processing means 26 are provided for analysing the signal from the detector 25 and displaying it. If a non-zero signal is produced by the processing means 26, a CVD material zone is assumed to be in contact with the end of the probe 23. Means may be provided for calibrating the apparatus, so that the signal displayed by the processing means 26 can be used diagnostically.

Applying the principle of reversability of light, it would also be possible for an illuminating means to be provided in the sphere instead of detector 25. Irradiating means 24 is then replaced by a detector for detecting the intensity of radiation transmitted through the zone of the diamond 20 in contact with the end of the fibre optic probe 23. If some transmission is observed, CVD diamond material is assumed to be present, whereas if no transmission is observed, natural diamond is assumed to be in contact with the end of the probe.

A reference reading may be provided by irradiating the diamond with radiation that is transmitted by both natural and synthetic diamond. A filter 30 may be provided in the filter wheel 28 to select, for example, the 365 nm band of the mercury lamp, which is substantially transmitted by all forms of diamond. The filter in front of the photo multiplier tube may also need to be changed.

Figure 8:
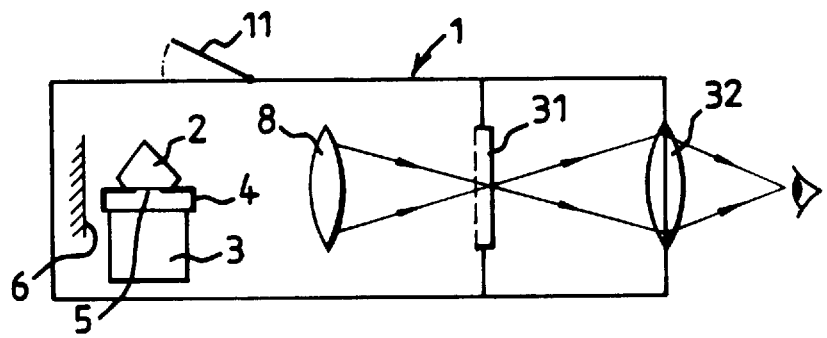
FIG. 8 shows a fifth embodiment of apparatus according to the invention.

FIG. 8 shows a fifth embodiment of an apparatus according to the invention. The apparatus is generally similar to that shown in FIG. 3, like parts of the apparatus being given like reference numerals. However, in the apparatus of FIG. 8, the lens system 8 focuses an image of the diamond 2 onto a ultraviolet conversion phosphor screen 31. The ultraviolet conversion phosphor screen 31 converts the ultraviolet image into a visible image. This visible image may be viewed using a further lens system 32, shown schematically. The image on screen 31 may be viewed by eye so that complex camera equipment is not required. However, in order to allow image processing, a camera system could be used to view the image on screen 31. The screen 31 and optical system 32 could be used in place of the camera and lens system 7, 8 and filter or image intensifier unit 14 of FIGS. 1, 3 or 4.

EXAMPLE

An apparatus was set up as shown in FIG. 3. The ultraviolet source 3 comprised a standard germicidal lamp (a low pressure mercury lamp, which produces a strong 254 nm line) manufactured by Philips, catalogue number TUV 6W. The lens system 8 comprised spectrosil B material lenses of 100 mm focal length, supplied by Comar Instruments, catalogue number 100 PS 25. The camera 7 comprised a ultraviolet sensitive Chalnicon TV (N983) tube installed in a Hamamatsu C1000 camera system.

The filter 9 comprises a ultraviolet solar blind filter manufactured by Corion.

The present invention has been described above purely by way of example, and modifications can be made within the invention. The invention also consists in any individual features described or implicit herein, or shown or implicit in the drawings or any combination of such features or any generalisation of any such features or combinations.

We claim:

1. A method of testing whether a diamond has a layer of synthetic diamond deposited thereon, comprising the steps of: irradiating at least two respective zones on the surface of the diamond with ultraviolet radiation; and observing the intensity of radiation having a wavelength substantially between 230 nm to 320 nm that is transmitted through each of said zones of the diamond to detect any reduced absorption of said transmitted radiation in at least a respective one of said zones which reduced absorption indicates that synthetic diamond is present in said zone.

2. The method of claim 1, wherein the radiation transmitted by the zones of the diamond is observed by forming an image of the diamond.

3. The method of claim 2, wherein a transmitted image of a first zone of the diamond is formed when the diamond is viewed in a first direction, and at least one further image of a second zone of the diamond is formed when the diamond is viewed in another direction.

4. The method of claim 1, wherein the radiation transmitted by a zone of the diamond is observed by using radiation collecting means and a detector.

5. The method of claim 4, wherein the diamond is placed in an integrating enclosure, said radiation is delivered to the integrating enclosure with the diamond being mounted so that said radiation must pass through a selected one of said zones of the diamond before reaching the detector which generates a signal representative of the intensity of the radiation transmitted through said zone.

6. The method of claim 1, wherein said transmitted light forms an image of the diamond against a light background.

7. The method of claim 2, wherein said transmitted light forms an image of the diamond against a dark background.

8. The method of claim 1, wherein at least one of said zones of the diamond is irradiated from a first direction to form an image of the diamond, and a further image of another zone is formed when the diamond when irradiated in a different direction.

9. The method of claim 1, further comprising irradiating each of a plurality of zones of the diamond with further radiation having a wavelength which is substantially transmitted by all types of diamond or which is substantially absorbed by all types of diamond, and comparing the intensity of said transmitted radiation of the first mentioned wavelength with the intensity of transmitted radiation of the further wavelength.

10. The method of claim 9, wherein an image of radiation of the further wavelength transmitted by the diamond is formed.

11. The method of claim 9, wherein the further radiation comprises visible radiation.

12. The method of claim 1, further comprising the step of identifying the diamond as a wholly natural diamond if all zones of the diamond strongly absorb radiation substantially of wavelength substantially 230 nm to 320 nm.

13. The method of claim 1, wherein the diamond is irradiated with radiation of the 254 nm band of a mercury lamp.

14. The method of claim 1, further comprising the step of identifying zones of the stone comprising CVD diamond material on the basis of whether such zones transmit the first mentioned radiation more strongly than other zones.

15. The method of any of claim 2, wherein the image is formed on a phosphorescent screen and observed by eye.

16. Apparatus for testing whether a diamond has a layer of synthetic diamond deposited thereon, comprising:

means for irradiating at least two respective zones on a surface of the diamond with ultraviolet radiation; and means for observing the intensity of radiation having a wavelength substantially between 230 nm to 320 nm that is transmitted through each of said zones to detect any reduced absorption of said transmitted radiation in at least one of said zones of the diamond which reduced absorption indicates the presence of synthetic diamond material in said zone.

17. The apparatus of claim 16, wherein said observing means, said at least one zone and said irradiating means are arranged generally on a straight line for imaging the diamond against a light background.

18. The apparatus of claim 16, wherein the axis of the irradiating means is substantially different from the optical axis of the imaging means for imaging the diamond against a dark background.

19. The apparatus of claim 18, wherein the irradiating means comprises means for confining the irradiating radiation, so that the radiation must pass through the diamond before entering the imaging means.

20. The apparatus of claim 16, further comprising mounting means for alterably mounting the diamond in a plurality of positions with respect to the irradiating means.

21. The apparatus of claim 16, wherein the irradiating means comprises means for irradiating the diamond with further radiation of a wavelength which is substantially transmitted by all types of diamond, or substantially absorbed by all types of diamond.

22. The apparatus of claim 21, wherein the further radiation comprises visible radiation.

23. The apparatus of claim 16, wherein the imaging means comprises an ultraviolet sensitive camera and display means.

24. The apparatus of claim 16, wherein the imaging means comprises means for forming the image on a phosphorescent screen, the phosphorescent screen being observable by eye.

25. The apparatus of claim 19, wherein the means for confining the irradiating radiation comprises a light guide such as a fibre optic probe.

26. Apparatus for testing whether a diamond has a layer of synthetic diamond deposited thereon, comprising: an integrating enclosure having irradiating means and means for mounting a diamond in a position such that radiation emitted from the irradiating means passes through at least a zone of the diamond before reaching detecting means, the detecting means for measuring the intensity of a portion of the radiation emitted by the irradiating means whose wavelength is substantially between 230 nm to 320 nm and that is transmitted by the zone to detect any reduced absorption of said transmitted radiation said zone, which reduced absorption indicates the presence of synthetic diamond material in said zone.

* * * * *